United States Patent [19]

Wess et al.

[11] Patent Number: 4,665,080
[45] Date of Patent: May 12, 1987

[54] IMIDAZOLYL COMPOUNDS AND THEIR USE AS MEDICAMENTS

[75] Inventors: Günther Wess, Erlensee; Wilhelm Bartmann, Bad Soden am Taunus; Gerhard Beck, Frankfurt am Main; Hans-Hermann Lau, Bad Soden am Taunus, all of Fed. Rep. of Germany

[73] Assignee: Hoechst Aktiengesellschaft, Frankfurt, Fed. Rep. of Germany

[21] Appl. No.: 751,550

[22] Filed: Jul. 3, 1985

[30] Foreign Application Priority Data

Jul. 6, 1984 [DE] Fed. Rep. of Germany ....... 3424944

[51] Int. Cl.$^4$ .................. C07D 401/12; C07D 233/54; A61K 31/415
[52] U.S. Cl. .................................... 514/341; 514/397; 514/399; 546/278; 548/335; 548/336
[58] Field of Search ................ 548/335, 336; 546/278; 514/341, 397, 399

[56] References Cited

U.S. PATENT DOCUMENTS 4,226,878 10/1980 Iizuka et al. .................. 548/335
4,555,516 11/1985 Cross et al. .................. 548/335

FOREIGN PATENT DOCUMENTS 0106060 4/1984 European Pat. Off. .

OTHER PUBLICATIONS

Fukumori et al., CA 101:396n.
Kaname et al., CA 98:22268u.
Iizuka et al., J. Med. Chem., 1981, 24, 1939–1948.

Primary Examiner—Jane T. Fan
Attorney, Agent, or Firm—Finnegan, Henderson, Farabow, Garrett & Dunner

[57] ABSTRACT

The present invention relates to new ortho-, meta- and para-substituted imidazolylmethylstyrenes of the formula I

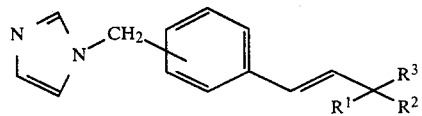

and to a process for their preparation.

The compounds according to the invention are distinguished by having a specific inhibitory effect on the synthesis of thromboxane, and hence they can be used as medicaments.

5 Claims, No Drawings

IMIDAZOLYL COMPOUNDS AND THEIR USE AS MEDICAMENTS

Imidazole and its derivatives substituted in position 1 are inhibitors of thromboxane synthetase (H.-H. Tai, Biochem. and Biophys. Res. Comm. 80, 236 (1978)).

Within the metabolism of arachidonic acid, the enzyme thromboxane synthetase catalyzes the conversion of prostaglandin endoperoxides ($PGH_2$ and $PGG_2$) into thromboxane $A_2$ ($TXA_2$). $TXA_2$ has high biological activity: it induces the aggregation of blood platelets and, moreover, has a potent constricting effect on smooth muscle. It plays an important part in hemostasis and in pathological situations where there is an increased tendency to vasospasms and/or thrombosis. Furthermore, $TXA_2$ has potent contracting effects on bronchial muscle in vitro and in vivo (B. Samuelsson, Angew. Chem. 95, 854 (1983)).

The new 1-imidazolylmethylstyrenes which are described in the present invention are distinguished by a specific inhibitory effect on thromboxane synthetase.

Thus they are suitable for the prophylaxis or treatment of disorders where there is a disturbance (an increase) in the tendency to platelet aggregation, and where there are pathologically raised levels of thromboxane, such as are found with ischemia, angina pectoris, thromboembolic diseases, atherosclerosis, coronary spasms, arrhythmias, cerebral ischemic attacks, migraine and other vascular headaches, myocardial infarct, hypertension, respiratory disturbances, such as asthma and apnea, inflammatory disorders, and microvascular complications associated with diabetes mellitus. The compounds according to the invention have favorable effects on diseases where there are raised levels of thromboxane in various organs, for example in the kidneys or the stomach and intestines with colitis or "inflammatory bowel disease". Furthermore, the compounds are suitable to slow down or prevent the proliferation of tumor cells.

The present invention relates to new ortho-, meta- and para-substituted imidazolylmethylstyrenes of the formula I

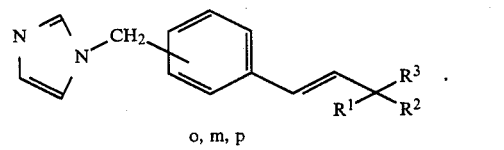

o, m, p

In the general formula I:
$R^1$ and $R^2$ together denote the carbonyl group, or $R^1$ denotes hydrogen, and $R^2$ denotes the radical —$OR^4$, in which $R^4$ represents hydrogen, or
(a) a branched or unbranched aliphatic acyl radical having up to 10 carbon atoms,
(b) the benzylcarbonyl or benzoyl radical, the phenyl radical being unsubstituted or substituted once to three times with halogen or $C_1$–$C_4$-alkyl,
(c) the radical

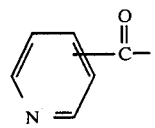

(d) branched or unbranched alkyl having 1–10 carbon atoms,
(e) the phenyl radical, the phenyl nucleus being unsubstituted or substituted once to three times with halogen or $C_1$–$C_4$-alkyl, or
(f) the radical

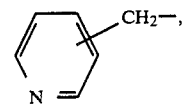

$R^3$ denotes a phenyl radical which can be substituted once to three times in the nucleus with halogen, trifluoromethyl and/or alkyl or alkoxy, each having 1–4 carbon atoms, or a cycloaliphatic radical having 3–8 carbon atoms, a straight-chain or branched alkyl radical having up to 8 carbon atoms, a straight-chain or branched unsaturated aliphatic hydrocarbon radical having 3 to 8 carbon atoms it being possible for the aliphatic radicals in turn to be substituted with
(a) a straight-chain or branched alkoxy radical having up to 10 carbon atoms, or a cycloalkoxy radical having up to 6 carbon atoms, or a straight-chain or branched alkenyloxy or alkynyloxy radical having 3 to 6 carbon atoms,
(b) halogen, cycloalkyl having 3–7 carbon atoms, an unsubstituted phenyl, α- or β-thienyl or α- or β-furyl radical or a phenyl, thienyl or furyl radical, which in turn are substituted once to three times in the nucleus with halogen, trifluoromethyl and/or alkyl or alkoxy having 1–4 carbon atoms,
(c) an unsubstituted phenoxy, α- or β-thienyloxy or cycloalkoxy radical having 3–7 carbon atoms, or one of the radicals mentioned which in turn is substituted once to three times in the nucleus with halogen, trifluoromethyl and/or alkyl or alkoxy each having 1–4 carbon atoms, or
(d) a heteroaryl radical.

The preferred meanings for the substituents are as follows:
$R^1$ and $R^2$ together are the carbonyl group, or $R^1$ is hydrogen and $R^2$ is the radical —$OR^4$, in which $R^4$ represents hydrogen, or
(a) branched or unbranched alkanoyl having up to 6 carbon atoms,
(b) the benzylcarbonyl or benzoyl radical, the phenyl nucleus being unsubstituted or substituted once with fluorine, chlorine or methyl,
(c) the radical

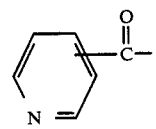

(d) branched or unbranched alkyl having 1–6 carbon atoms,
(e) the benzyl radical, the phenyl nucleus being unsubstituted or substituted once with chlorine, fluorine or methyl, or
(f) the radical

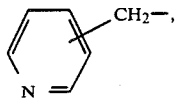

and $R^3$ is a cycloaliphatic radical having 3–8 carbon atoms, a straight-chain or branched alkyl radical having up to 8 carbon atoms, a straight-chain or branched unsaturated aliphatic hydrocarbon radical having 3 to 8 carbon atoms, it being possible for the aliphatic radicals in turn to be substituted with
 (a) a straight-chain or branched alkoxy radical having up to 6 carbon atoms, or a cycloalkoxy radical having up to 6 carbon atoms, or a straight-chain or branched alkenyloxy or alkynyloxy radical having 3 to 6 carbon atoms,
 (b) cycloalkyl having 3–7 carbon atoms, an unsubstituted phenyl, α- or β-thienyl or α- or β-furyl radical,
 (c) an unsubstituted phenoxy, α- or β-thienyloxy or cycloalkoxy radical having 3–7 carbon atoms, or one of the radicals mentioned which in turn is substituted once to three times in the nucleus with halogen, trifluoromethyl and/or alkyl or alkoxy each having 1–4 carbon atoms, or
 (d) a heteroaryl radical.

The following substituents are particularly preferred: $R^1$ and $R^2$ are together the carbonyl group, or $R^1$ is hydrogen, and $R^2$ is the radical —$OR^4$, in which $R^4$ represents hydrogen, benzyl, alkyl having 1–6 carbon atoms or the radical

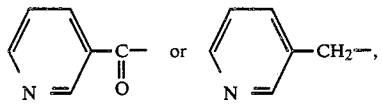

$R^3$ is a cycloaliphatic radical having 3–8 carbon atoms, a straight-chain or branched alkyl radical having up to 8 carbon atoms, a straight-chain or branched unsaturated aliphatic hydrocarbon radical having 3 to 8 carbon atoms, it being possible for the aliphatic radicals in turn to be substituted with
 (a) a straight-chain or branched alkoxy radical having up to 10 carbon atoms,
 (b) cycloalkyl having 3–7 carbon atoms, an tuted phenyl, α- or β-thienyl or α- or β-furyl radical, or a phenyl, thienyl or furyl radical,
 (c) an unsubstituted phenoxy, α- or β-thienyloxy or cycloalkoxy radical having 3–7 carbon atoms, or
 (d) a 1-imidazolyl radical, in particular the radicals: n-pentyl, 1,1-dimethylpentyl, cyclopentylmethyl, cyclohexylmethyl, methoxymethyl, ethoxymethyl, propoxymethyl, butoxymethyl, pentoxymethyl, hexyloxymethyl, heptyloxymethyl, cyclopentyloxymethyl, cyclohexyloxymethyl, dimethylpentoxymethyl, 1,1-dimethyl-2-ethoxymethyl, phenoxymethyl, 2ethoxyethyl, 2-butoxyethyl, 3-ethoxypropyl, 5-methoxypentyl, (2-ethoxy)ethoxymethyl, 3-chlorophenoxymethyl, 1,1-dimethyl-2-benzyloxyethyl, 3-methoxycarbonylpropyl, 4-methoxycarbonylbutyl, 5-methoxycarbonylpentyl, 3-carboxypropyl, 4-carboxybutyl, 5-carboxypentyl, 4-(3-chlorobenzyloxy)phenyl, phenylethoxymethyl, 3-thienyloxymethyl, 2-thienyloxymethyl, 2-(1-imidazolyl)ethyl and dimethyl-(1-imidazolyl).

The invention also relates to acid addition salts with inorganic or organic acids, for example hydrochloric acid, hydrobromic acid, sulfuri acid, phosphoric acid or nitric acid, acetic acid, propionic acid, oxalic acid, malonic acid, glycolic acid, succinic acid, maleic acid, fumaric acid, malic acid, tartaric acid, citric acid, benzoic acid or cinnamic acid.

The invention also relates to a process for the preparation of the compounds of the general formula I, which comprises
(a) reaction of the appropriate ortho-, meta- and para-substituted 1-imidazolylmethylbenzaldehydes of the formula II

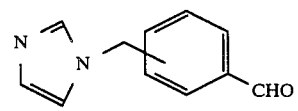

by the method of Horner-Emmons-Wittig with a phosphonic ester of the general formula III

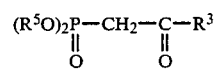

$R^3$ having the meaning indicated in the general formula I, and $R^5$ denoting $C_1$–$C_4$-alkyl, to give the compounds according to the invention, of the general formula IV

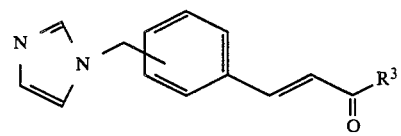

$R^3$ having the meaning indicated for formula I,
(b) where appropriate reducing the enones of the general formula IV with a reducing agent to give the alcohols according to the invention, of the general formula V

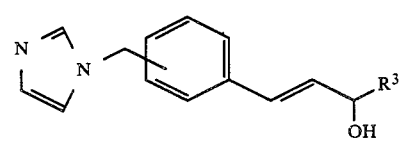

in which $R^3$ has the meaning given for formula I,
(c) where appropriate converting the alcohols of the formula V, in the form of their racemates or as pure enantiomers, using a reactive derivative of a carboxylic acid to give the esters according to the invention, of the general formula VI

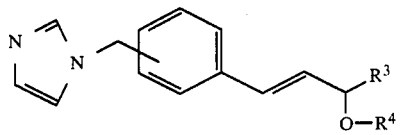

in which R³ has the meaning given for formula I, and R⁴ denotes a branched or unbranched aliphatic acyl radical having up to 10 carbon atoms, or the benzylcarbonyl or benzoyl radical, in which the phenyl nucleus can be substituted once to three times with halogen or $C_1$–$C_4$-alkyl, or the radical

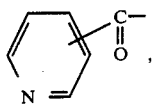

or (d) where appropriate converting the alcohols of the formula V, in the form of their racemates or as pure enantiomers, using an appropriate halide, tosylate or mesylate, into the ethers according to the invention, of the general formula VII

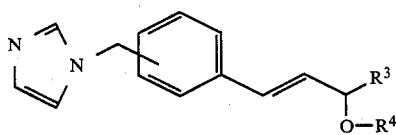

in which R⁴ represents $C_1$–$C_{10}$-alkyl, benzyl in which the phenyl nucleus can be substituted once to three times with halogen or $C_1$–$C_6$-alkyl, or the radical

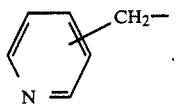

In order to prepare the 1-imidazolylmethylbenzaldehydes of the formula II, which are used as starting material in the process according to the invention, the corresponding chloromethylbenzaldehydes, or their acetals, are reacted with imidazole in the presence of a base. A preferred embodiment comprises reaction of the ethylene acetals of the o-, m- and p-chloromethylbenzaldehydes with imidazole in toluene as the solvent, using potassium carbonate as the base, at a suitable temperature, preferably at the reflux temperature.

The chloromethylbenzaldehydes can be prepared in analogy to known processes (for example R. Grice, L. N. Owen, J. Chem. Soc. 1963, 1947 or I. W. Baker, I. A. L. Brieux, D. G. Saunders, J. Chem. Soc. 1956, 404).

The o-, m- and p-(1-imidazolylmethyl)benzaldehydes of the formula II are reacted by the method of Horner-Emmons-Wittig with a phosphonic ester of the general formula III, a preferred embodiment comprising allowing the phosphonic esters of the formula III to react with the aldehyde of the formula II in dimethoxyethane using DBU (1,8-diazabicyclo[5.4.0]undec-7-ene) as the base, at room temperature up to the reflux temperature, for 1–36 hours.

The phosphonic esters of the formula III can be prepared by processes known from the literature (see, for example, J. Am. Chem. Soc. 88, 5654 (1966)).

The alcohols of the general formula V are obtained in the form of their racemates when an enone of the general formula IV is reduced with a complex metal hydride, preferably with an alkali metal boranate, preferably between −10° C. and room temperature, in methanol, ethanol or ethers such as DME and THF, where appropriate with the addition of water.

The acylation of the alcohols of the formula V to give the esters of the formula VI is carried out in a generally customary manner using acyl halides (such as, for example, nicotinoyl chloride) or with acid anhydrides in the presence of bases, such as pyridine and triethylamine, inter alia.

The etherification of the alcohols of the formula V to give the ethers of the formula VI is carried out in the generally customary manner using halides (such as, for example, benzyl halide), mesylates or tosylates, in the presence of bases such as, for example, sodium hydride, in suitable solvents such as, for example, DMF.

Where the individual reaction products do not result in a form sufficiently pure to be used immediately for the subsequent reaction step, it is advisable to carry out purification by crystallization or column, thin-layer or high-pressure liquid chromatography.

The acid addition salts of compounds of the general formula I are obtained by addition of the appropriate inorganic or organic acids, usually in the form of a solution, to solutions of the appropriate imidazole compound of the general formula I. Examples of solvents which are used are water, alcohols as well as various ethers and esters.

Apart from the compounds described in the examples, the following compounds can be prepared by the process according to the invention:

E-4-ethoxy-1-[4-(1-imidazolylmethyl)phenyl]but-1-en-3-ol, E-5-ethoxy-1-[4-(1-imidazolymethyl)phenyl]pent-1-en-3-ol, E-5-butoxy-1-[4-(1-imidazoilylmethyl)phenyl]pent-1-en-3-ol, E-6-ethoxy-1-[4-(1-imidazolylmethyl)phenyl]hex-1-en-3-one, E-6-ethoxy-1-[4-(1-imidazolylmethyl)phenyl]hex-1-en-3-ol, E-7-methoxy-1-[4-(1-imidazolylmethyl)phenyl]hept-1-en-3-one, E-7-methoxy-1-[4-(1-imidazolylmethyl)phenyl]hept-1-en-3-ol, E-8-methoxy-1-[4-(1-imidazolylmethyl)phenyl]oc-1-en-3-one, E-8-methoxy-1-[4-(1-imidazolylmethyl)phenyl]oct-1-en-3-ol, E-5-(1imidazolyl)-1-[4-(1-imidazolylmethyl)phenyl]pent-1-en-3-ol, E-4,4-dimethyl-4-(1-imidazolyl-1-[4-(1-imidazolylmethyl)phenyl]but-1-en-3-one, E-4,4-dimethyl-4-(1-imidazolyl)-1-[4-(1-imidazolylmethyl)phenyl]but-1-en-3-ol, E-3-(3-chlorophenyl)-1-[4-(1-imidazolylmethyl)phenyl]prop-1-en-3-one and E-3-(3-chlorophenyl)-1-[4-(1-imidazolylmethyl)phenyl]prop-1-en-3-ol and the nicotinic esters, benzyl ethers and (3-pyridyl)methyl ethers of the alcohols listed here and in Table 2.

The compounds of the formula I are distinguished by having a specific inhibitory effect on thromboxane synthetase, and they can thus be used as medicaments for the prophylaxis or treatment of disorders where there is a disturbance (an increase) in the tendency to platelet aggregation, and where there are pathologically raised levels of thromboxane, such as are found with ischemia, angina pectoris, thromboembolic diseases, atherosclerosis, coronary spasms, arrhythmias, cerebral ischemic attacks, migraine and other vascular headaches, myocardial infarct, hypertension, respiratory disturbances, such as asthma and apnea, inflammatory disorders, and microvascular complications associated with diabetes mellitus. The compounds according to the invention have favorable effects on diseases where there are raised levels of thromboxane in various organs, for example in the kidneys or the stomach and intestines with colitis or "inflammatory bowel disease." Furthermore, the compounds are suitable to slow down or prevent the proliferation of tumor cells. The compounds can be administered in daily doses of 0.01 mg/kg to 10 mg/kg, preferably 0.1 mg/kg to 5 mg/kg, and in single doses of 0.01 mg/kg to 7.5 mg/kg, preferably 0.1 mg/kg to 2.5 mg/kg.

Metabolites of arachidonic acid are involved in a large number of physiological and pathophysiological processes. Prostacyclin ($PGI_2$) and thromboxane $A_2$ ($TXA_2$) play an essential part in the regulation of the tone of blood vessels and of aggregration of blood platelets. Prostacyclin, which is produced from prostaglandin endoperoxide $H_2$ ($PGH_2$) preferentially in the endothelial cells of the blood vessels, has a vasodilator effect and prevents the aggregation of blood platelets. The conversion of prostaglandin endoperoxide into prostacyclin is catalyzed by the enzyme prostacyclin synthetase. Thromboxane $A_2$ is the physiological antagonist of prostacyclin. It is produced from $PGH_2$, mainly in the blood platelets. The enzyme thromboxane synthetase catalyzes this reaction. $TXA_2$ brings about aggregation of blood platelets and leads to vasoconstriction. As far as is known, thromboxane is the most potent vasoconstrictor in the human body (A. G. Herman, P. M. Vonhoutte, H. Denolin, A. Goossens, Cardiovascular Pharmacology of the Prostaglandins, Raven Press, New York 1982). Imbalances between prostacyclin and thromboxane $A_2$ lead to pathophysiological situations. A shift in the equilibrium in favor of thromoboxane thus leads to platelet aggregation and vasospasms and to an increased susceptibility to atherothrombosis (Lancet 1977, 479; Science 1976, 1135; Amer. J. Cardiology 41, 787 (1978); Lancet 1977, 1216). In experimental atherosclerosis, the formation of $PGI_2$ is suppressed and the formation of $TXA_2$ is raised (Prostaglandins 14, 1025 and 1035 (1977)). For this reason, thromboxane $A_2$ has been connected with various types of angina, formation of myocardial infarcts, sudden heart death and strokes (Thromb. Haemostasis 38, 132 (1977); Platelets, Prostaglandins and Cardiovascular System, Florence, February 1984).

Another area in which an imbalance of $PGI_2$ and $TXA_2$ is regarded as a contributory factor is that of migraine. Migrainous headache is connected with changes in the intra- and extra-cerebral blood flow, in particular with a reduction, which takes place before the occurrence of the headache, in the cerebral blood flow and subsequent dilatation in both vascular regions during the headache phase. Blood platelets from migraine patients have a greater tendency to aggregation than do those from normal individuals (J. clin. Pathol. 24, 250 (1971); J. Headache, 17, 101 (1977); Lancet 1978, 501).

In patients with diabetes mellitus, an imbalance between prostacyclin and thromboxane $A_2$ is regarded as being responsible for the microvascular complications. Platelets from diabetic patients form increased amounts of $TXB_2$ and malondialdehyde, see the symposium "Diabetes and Thrombosis—Implications for Therapy", Leeds, Great Britain (April 1979). Furthermore, it has been shown that the vascular formation of prostacyclin is inhibited in rats with experimentally induced diabetes, and the $TXA_2$ synthesis from the platelets is raised, see Ivth International Prostaglandin Conference, Washington, D.C. (May 1979).

Non-steroidal antiinflammatory agents inhibit cyclooxygenase, which catalyzes the conversion of arachidonic acid into $PGH_2$ via $PGG_2$. Thus, they intervene not only in the biosynthesis of thromboxane but also in the biosynthesis of prostacyclin. Thus, a compound which specifically inhibits the formation of $TXA_2$ by blockade of $TXA_2$ synthetase and leaves the prostacyclin route unaffected would be more valuable.

Thus the compounds of the formula I are suitable for the prophylaxis or treatment of the abovementioned diseases which respond to inhibition of thromboxane synthetase.

The compounds of the formula I are administered in various dosage forms, for example orally in the form of tablets, capsules or liquids, rectally in the form of suppositories, parenterally, subcutaneously or intramuscularly, and intravenous administration being preferred in emergency situations.

The compounds according to the invention, of the formula I, can be used as free bases or in the form of their physiologically acceptable inorganic or organic acid addition salts. The free bases and acid addition salts can be used in the form of their aqueous solutions or suspensions as well as dissolved or suspended in pharmacologically acceptable organic solvents, such as monohydric or polyhydric alcohols such as, for example, ethanol, ethylene glycol or glycerol, in triacetin, in alcohol/acetaldehyde diacetal mixtures, oils such as, for example, sunflower oil or fish liver oil, ethers such as, for example, diethylene glycol dimethyl ether, as well as polyethers such as, for example, polyethylene glycol, as well as in the presence of other pharmacologically acceptable polymeric vehicles such as, for example, polyvinylpyrrolidone.

Suitable possible formulations are the customary pharmaceutical solutions for infusion or injection, and tablets, as well as formulations which can be applied topically, such as creams, emulsions, suppositories or aerosols.

EXAMPLE 1a 4-(1-Imidazolylmethyl)benzaldehyde ethylene acetal 54 g (0.27 mol) of 4-chloromethylbenzaldehyde ethylene acetal, 20 g (0.29 mol) of imidazole and 70 g (0.5 mol) of potassium carbonate were heated, while stirring, in 800 ml of toluene to reflux for 2 h. After cooling, about 500 ml of water were added and the mixture was stirred vigorously at room temp. for 15 min. The phases were separated and the aqueous phase was extracted 2x with toluene. Drying of the combined organic phases over magnesium sulfate and removal of the solvent in vacuo resulted in a yellowish oil which was chromatographed over a short silica gel column (chloroform/methanol=10:1). Yield: 44.3 g (0.192 mol, 71%) as a yellowish oil.

$^1$H-NMR (CDCl$_3$, 60 MHz) δ=4.0 (m, 4H, —OCH$_2$CH$_2$O—), 5.1 (s, 2H, —CH$_2$—), 5.8 (s, 1H, methyne-H), 6.8-7.7 (m, 7H, arom. H)

1b: 2-(1-Imidazolylmethyl)benzaldehyde ethylene acetal is obtained in analogy to 1a.

$^1$H-NMR (CDCl$_3$, 60 MHz) δ=4.0 (m, 4H, —OCH$_2$CH$_2$O—), 5.2 (s, 2H, —CH$_2$—), 5.7 (s, 1H, methyne-H), 6.7-7.9 (m, 7H, arom. H).

1c: 3-(1-Imidazolylmethyl)benzaldehyde ethylene acetal is obtained in analogy to 1a.
$^1$H-NMR (CDCl$_3$, 60 MHz); δ=4.1 (m, 4H, —OCH$_2$CH$_2$—O), 5.0 (s, 2H, —CH$_2$—), 5.8 (s, 1H, methyne-H), 6.7-7.7 (m, 7H, arom. H).

EXAMPLE 2a

Preparation of 4-(1-imidazolylmethyl)benzaldehyde
44.3 g (0.192 mol) of 4-(1-imidazolylmethyl)benzaldehyde ethylene acetal were stirred in 450 ml of 1N aqueous hydrochloric acid at room temp. for 3.5 h. The mixture was neutralized with saturated aqueous sodium bicarbonate solution, saturated with sodium chloride and extracted three times with toluene. The combined organic phases were dried over magnesiun sulfate. Removal of the solvent in vacuo produced 27.1 g (0.146 mol, 76%) of the aldehyde as yellowish oil.
IR (film): 1700 cm$^{-1}$ (s, carbonyl),
δ=5.2 (s, 2H, —CH$_2$—), 6.8-7.9 (m, 7H, arom. H), 9.9 (s, 1H, —CHO)
2b: 2-(1-Imidazolylmethyl)benzaldehyde is obtained in analogy to 2a:
$^1$H-NMR (CDCl$_3$, CDCl$_3$) δ=5.55 (s, 2H, —CH$_2$—) 6.8-7.9 (m, 7H, arom. H), 9.9 (s, 1H, —CHO)
2c: 3-(1-Imidazolylmethyl)benzaldehyde is obtained in analogy to 2a.
$^1$H-NMR (CDCl$_3$, 60 MHz), δ=5.3 (s, 2H, —CH$_2$—), 6.7-7.9 (m, 7H, arom. H), 9.8 (s, 1H, —CHO)

EXAMPLE 3

Dimethyl 2-oxo-3-pentyloxypropanephosphonate
25.6 g (0.2 mol) of dimethyl methanephosphonate in 200 ml of dry tetrahydrofuran were initially introduced under an atmosphere of argon. 250 ml of a 1.6 molar solution of butyllithium in hexane (0.4 mol) and 100 ml of a solution of 32.04 g (0.2 mol) of methyl 2-pentyloxyacetate in tetrahydrofuran were introduced into separate dropping funnels. Then, at −70° C. to −65° C., 125 ml of the butyllithium solution and, immediately thereafter, 50 ml of the ester solution were added dropwise. The mixture was stirred at −70° C. for 1 h and then a further 63 ml of the butyllithium solution and 25 ml of the ester solution were added dropwise at −70° C., and the mixture was stirred at this temperature for 1 h. Finally, the remaining 62 ml of the butyllithium solution and 25 ml of the ester solution were added dropwise at the same temp. and the mixture was stirred for 2 h. It was allowed to stand overnight in dry ice. For working-up, the pH of the solution was adjusted to 5, at 0°-5° C., with about 160 ml of 2N aqueous hydrochloric acid, and then the THF was removed in a rotary evaporator. The residue was taken up in saturated aqueous sodium chloride solution, and the solution was extracted four times with ethyl acetate. Drying of the combined ethyl acetate phases over magnesium sulfate, removal of the solvent in vacuo and fractional distillation produced 37.0 g (0.147 mol, 73%) of phosphonate as a colorless liquid, boiling point 130°-132° C./0.5 Torr.
IR (film): 1730 cm$^{-1}$ (s, carbonyl)
$^1$H-NMR (60 MHz, CDCl$_3$): δ=0.8-1.8 (m, 9H, —(CH$_2$)$_3$CH$_3$), 3.16 (d, J=22 Hz, 2H, P—CH$_2$—), 3.47 (t, J=6 Hz, 2H, —OCH$_2$—) 3.75 (d, J=11 Hz, 6H, —OCH$_3$), 4.1 (s, 2H, —CH$_2$—)
The phosphonates of the formula III are obtained in analogy to Example 3. The esters used as starting material are substantially known from the literature or are prepared in analogy to known processes.

EXAMPLE 4a

E-4-Pentyloxy-1-[4-(1-imidazolylmethyl)phenyl]but-1-en-3-one
2 g (7.93 mmol) of dimethyl 2-oxo-3-pentyloxypropanephosphonate, 1.7 g (9.13 mmol) of 4-(1-imidazolylmethyl)benzaldehyde and 1.33 g (8.74 mmol) of DBU were stirred in 150 ml of dimethoxyethane at room temperature for 31 h. The mixture was filtered through silica gel and the solvent was removed from the filtrate in vacuo. Chromatography on silica gel (chloroform/methanol/25% aqueous NH$_3$=20/1/0.2) produced 1.5 g (4.80 mmol, 60%) as a yellowish oil which solidified in the refrigerator, melting point 35°-36° C.
Rf=0.5
IR (film): 1690 cm$^{-1}$ (s), 1610 (s)
$^1$H-NMR (CDCl$_3$, 60 MHz) δ=0.7-2.0 (m, 9H, alkyl-H), 3.5 (t, 2H, —OCH$_2$—), 4.2 (s, 2H, —OCCH$_2$O—), 5.2 (s, 2H, N—CH$_2$—Ar), 6.7-8.0 (m, 9H, arom-H and vinyl-H).
Further compounds, inter alia the Examples 4b–4v listed in Tab. 1, are obtained in analogy to Example 4a.

TABLE 1

| Example | o,m,p R | R structure | characteristic $^1$H—NMR-signals (CDCl$_3$, 60 MHz), δ = | Rf. silica gel |
|---|---|---|---|---|
| 4b | para | (structure with —(CH$_2$)$_3$CH$_3$ chain) | 0,58-2,0 (m, 15H, methyl and —(CH$_2$)$_3$CH$_3$) | 0,24 CHCl$_3$/CH$_2$OH/ NH$_4$OH = 20:0,5:0,1 |
| 4c | para | (structure with phenoxy group) | 4,73 (s, 2H, —CH$_2$O—) | 0,21 CHCl$_3$/CH$_3$OH/ NH$_4$OH = 20:0,4:0,1 |

TABLE 1-continued

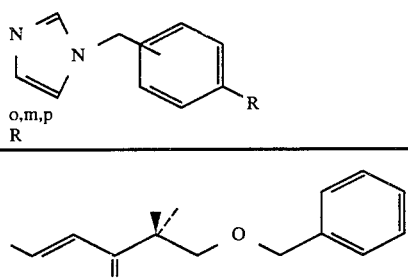

| Example | o,m,p R | characteristic $^1$H—NMR-signals (CDCl$_3$, 60 MHz), δ = | Rf. silica gel |
|---|---|---|---|
| 4d | 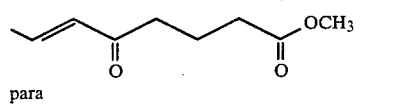 | 1,2(s,6H,CH$_3$)<br>3,5(s,2H,CH$_2$O)<br>4,5(s,2H,CH$_2$OC$_6$H$_5$)<br>5,1(s,2H,N—CH$_2$)<br>6,9-7,6(m,14H, aromat. prot.) | 0,46<br>CH$_2$Cl$_2$/MeOH = 20:1 |
| 4e | 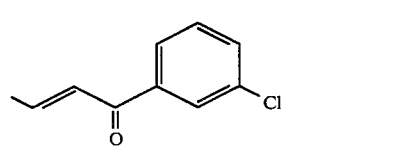<br>para | 1,9-2,9(m,6H, CH$_2$)<br>3,6(s,3H,OCH$_3$)<br>5,1(s,2H,N—CH$_2$)<br>6,5-7,7(m,9H, aromat. prot.) | 0,36<br>CH$_2$Cl$_2$/MeOH = 20:1 |
| 4f | 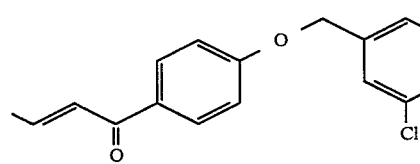 | 5,2(s,2H,CH$_2$)<br>6,9-8,0(m,13H, aromat. and olefin. prot.) | 0,2<br>ethyl acetate/ MeOH = 8:1 |
| 4g | 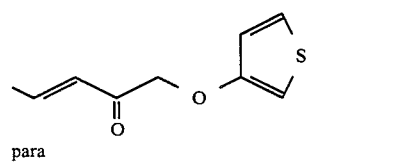<br>para | 5.1(s,2H, CH$_2$OC$_6$H$_4$Cl)<br>5.12(s,2H,NCH$_2$)<br>6,9-8,1(m,17H, olefinic and aromat. prot.) | 0,44<br>CHCl$_3$/MeOH = 9:1 |
| 4h | 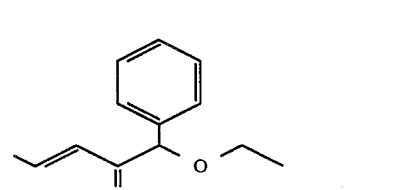<br>para | 4,8(s,2H, CH$_2$O—thiophene)<br>5.15(s,2H,CH$_2$N)<br>6,15-6,25(m,1H<br>6,8-7,9(m,11H,olefin + aromat. prot) | 0,22<br>CHCl$_3$/MeOH = 9:1 |
| 4i | 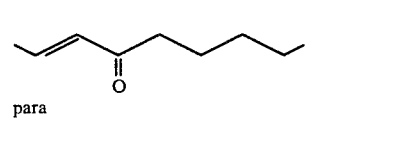<br>para | 1,2(t,3H,OC$_2$H$_5$)<br>3,5(q,2H,OC$_2$H$_5$)<br>5,1(s,2H,CH$_2$H)<br>6.9-8,0(m,14H olefin. + aromat. prot.) | 0,26<br>CHCl$_3$/MeOH = 9:1 |
| 4j | 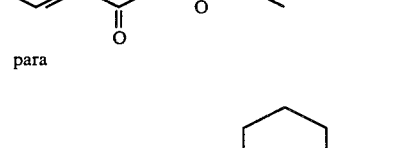<br>para | 0,6-2,1(m,9H, (CH$_2$)$_3$CH$_3$),<br>2,67(t,2H, —COCH$_2$—) | 0,16<br>ethyl acetate/ CH$_3$OH = 20:1 |
| 4k | 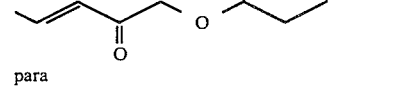<br>para | 1,33(t,3H,—CH$_3$)<br>3,63(q,2H,—CH$_2$—)<br>4,2(s,2H,—CH$_2$—) | 0,19<br>ethyl acetate/ CH$_3$OH = 20:1 |
| 4l | <br>para | 1,0-2,2(m,10H, Methylene-H),<br>3,33(m,1H, Methyne-H), 4,23 (s,2H,—OCH$_2$—) | 0,14<br>ethyl acetate/ CH$_3$OH = 20:1 |

TABLE 1-continued

| Example | o,m,p R | characteristic $^1$H—NMR-signals (CDCl$_3$, 60 MHz), δ = | Rf. silica gel |
|---|---|---|---|
| 4m | para | 1,23(t,3H,—CH$_3$) 3,33–3,66(m,6H, —CH$_2$—), 4,33 (s, 2H,—COCH$_2$O—) | 0,14 ethyl acetate/ CH$_3$OH = 20:1 |
| 4n | para | 3,1(t,2H,CH$_2$CO) 4,25(t,2H,NCH$_2$) 5,1(s,2H,NCH$_2$) 6,5–7,7(m,9H, olefin. + aromat. prot.) | 0,17 ethyl acetate/ CH$_3$OH = 2:1 |
| 4o | para | 0,8–1,6(m,7H, C$_3$H$_7$) 2,95(t,2H,CH$_2$CO) 3,2–3,95(t + q,4H, 2 × CH$_2$O) 5,1(s,NCH$_2$,2H) 6,5–7,8(m,9H, olefin + aromat. prot) | 0,31 ethyl acetate/ CH$_3$OH = 4:1 |
| 4p | para | 1,15(t,3H,OC$_2$H$_5$) 2,95(t,2H,CH$_2$CO) 3,25–3,9(t + q,4H, 2 × CH$_2$O) 5,1(s,2H,NCH$_2$) 6,5–7,9(m,9H, olefin + aromat. prot.) | 0,45 ethyl acetate/ CH$_3$OH = 4:1 |
| 4q | para | 0,9–1,9(m,9H, CH$_2$) 2,0(d,3H,CH$_3$) 2,8(t,2H,CH$_2$CO) 5,1(s,2H,N—CH$_2$) 6,9–7,7(m,9H, aromat. prot.) | 0,20 CH$_2$Cl$_2$/MeOH = 20:1 |
| 4r | ortho | 0,6–2,1 (m,15H,Methyl-H) and —(CH$_2$)$_3$CH$_3$ | 0,25 ethyl acetate/ CH$_3$OH = 20:1 |
| 4s | ortho | 0,8–2,1(m,9H, Alkyl-H) 3,5(t,2H,—OCH$_2$—) 4,2(s,2H, —OCCH$_2$O—) | 0,55 CHCl$_3$/CH$_3$OH/ 25 percent aq. . NH$_3$ = 20:1:0,2 |
| 4t | ortho | 1,2(s,6H,—CH$_3$), 3,5(s,2H,CH$_2$O), 4,5(s,2H, CH$_2$OC$_6$H$_5$) | 0,5 CH$_2$Cl$_2$/ CH$_3$OH = 20:1 |
| 4u | meta | 1,8–2,8(m,6H, CH$_2$), 3,6(s,3H, OCH$_3$) | 0,45 CH$_2$Cl$_2$/ CH$_3$OH = 20:1 |

TABLE 1-continued

| Example | o,m,p R | characteristic $^1$H—NMR-signals (CDCl$_3$, 60 MHz), δ = | Rf. silica gel |
|---|---|---|---|
| 4v | meta (cyclohexyloxy enone) | 1,0-2,2(m,10H, Methylene-H), 3,3(m,1H, Methyne-H), 4,2 (s,2H,—OCH$_2$—) | 0,25 ethyl acetate/ CH$_3$OH = 20:1 |

EXAMPLE 5a

E-4-Pentyloxy-1-[4-(1-imidazolylmethyl)phenyl]but-1-en-3-ol 61 mg (1.61 mmol) of sodium borohydride were added to 500 mg (1.60 mmol) of enone 4a in 10 ml of methanol, while cooling in ice. The mixture was stirred for 1 h while cooling in ice, and the reaction mixture was evaporated in vacuo, water was added to the residue and its pH was adjusted to 7 with 1N hydrochloric acid. The aqueous solution was saturated with sodium chloride and extracted four times with ethyl acetate. Washing of the combined organic phases with saturated sodium chloride solution and drying over magnesium sulfate produced, after removal of the solvent in vacuo, 400 mg (1.27 mmol, 79%) of a colorless oil.

Rf: 0.30 (CHCl$_3$/methanol/25 percent aqueous NH$_3$=20/1/0.2)

IR. (Film) 3250 cm$^{-1}$ (s)

$^1$H-NMR (CDCl$_3$, 60 MHz) δ=0.6–2.0 (m, 9H, alkyl-H), 2.7 broad, 1H, OH), 3.3–3.8 (m, 4H, —CH$_2$OCH$_2$—), 4.2–4.7 (m, 1H, methyne-H), 5.1 (s, 2H, N—CH$_2$—Ar), 6.0–7.6 (m, 9H, arom-H and vinyl-H).

Further commpounds, inter alia the Examples 5b5j listed in Tab. 2, are obtained in analogy to Example 5a.

TABLE 2

| Example | R | characteristics $^1$H—NMR— signals (CDCl$_3$, 60 MHz), δ = | Rf silica gel |
|---|---|---|---|
| 5b | para (phenoxy allylic alcohol) | 4,0 (m,2H, —CH$_2$O—), 4,67 (m,1H, Methyne-H), | 0,20 CHCl$_3$/CH$_3$OH = 9:1 |
| 5c | para (benzyloxy branched allylic alcohol) | 0,95(d,6H,CH$_3$) 3,4(d,2H,CH$_2$O) 4,5(s,2H,CH$_2$OC$_6$H$_5$) 5,05(s,2H,N—CH$_2$) 6,0-7,6(m,14H, aromat. and olefin. prot.) | 0,28 CH$_2$Cl$_2$/ MeOH = 20:1 |
| 5d | para (3-chlorophenyl allylic alcohol) | 5,1(s,2H,CH$_2$), 5,35(d,1H,CH—O), 6,1-6,45(dd,1H, =CH—CHO) 6,7(d,1H,=CH—Ph) 6,9-7,6(m,11H, aromat. H) | 0,29 ethyl acetate/ CH$_3$OH = 8:1 |
| 5e | para (cyclohexyloxy allylic alcohol) | 1,0-2,3(m,10H, Methylene-H), 4,5(m,1H, Methyne-H) | 0,32 CHCl$_3$/CH$_3$OH = 9:1 |

TABLE 2-continued

Structure: imidazole-N-CH2-phenyl-R (1-[(4-R-benzyl)]imidazole framework)

| Example | R | characteristics $^1$H—NMR— signals (CDCl$_3$, 60 MHz), δ = | Rf silica gel |
|---|---|---|---|
| 5f | CH3-CH=CH-CH(OH)-CH2-O-CH2CH2-O-CH2CH3 (para) | 1,23(t,3H,CH$_3$), 3,33–3,91(m,8H, —CH$_2$—), 4,5(m, 1H, Methyne-H) | 0,42 CHCl$_3$/CH$_3$OH = 9:1 |
| 5g | CH3-CH=CH-CH(OH)-CH2-O-phenyl (ortho) | 4,0(m,2H,—CH$_2$O—) 4,68(m,1H, Methyne-H) | 0,25 CHCl$_3$/CH$_3$OH = 9:1 |
| 5h | CH3-CH=CH-CH(OH)-CH2-O-(CH2)4-CH3 (ortho) | 0,7–2,0(m,9H, Alkyl-H), 3,3– 3,8(m,4H, —CH$_2$OCH$_2$—) 4,3–4,6(m,1H Methyne-H) | 0,35 CHCl$_3$/CH$_3$OH/ 25 percent aq. NH$_3$ = 20:1:0,2 |
| 5i | CH3-CH=CH-CH(OH)-(3-chlorophenyl) (meta) | 5,4(d,1H, Methyne-H), 6,9–7,6(m,11H, arom. H) | 0,3 ethyl acetate/ CH$_3$OH = 9:1 |
| 5j | CH3-CH=CH-CH(OH)-CH2-O-cyclohexyl (meta) | 1,0–2,3(m,10H, Methylene-H), 4,5(m,1H, Methyne-H) | 0,35 CHCl$_3$/CH$_3$OH = 9:1 |

EXAMPLE 6a

E-4-Pentyloxy-3-(3-pyridylcarbonyloxy)-1-[4-(1-imidazolylmethyl)phenyl]but-1-ene 400 mg (1.3 mmol) of E-4-pentyloxy-1-[4-(1-imidazolylmethyl)phenyl]but-1-en-3-ol (5a) were dissolved in 10 ml of dry pyridine, and 409 mg (1.5 mmol) of 3-pyridinecarbonyl chloride hydrochloride were added. The mixture was stirred at room temp. for 8 h, and the solvent was substantially removed in vacuo, and the residue was partitioned between saturated aqueous sodium bicarbonate solution and methylene chloride. The aqueous phase was extracted twice with methylene chloride. Drying of the combined organic phases with magnesium sulfate and removal of the solvent in vacuo produced, after chromatography on silica gel (ethyl acetate/methanol=10:1, Rf=0.20), 380 mg (0.91 mmol, 70%) of ester 6a as a colorless oil.

IR(film): 1720 cm$^{-1}$ (s, estercarbonyl)

$^1$H-NMR (60 MHz, CDCl$_3$): δ=0.70–1.8 (m, 9H, alkyl-H), 3.3–3.8 (m, 4H, —CH$_2$OCH$_2$—), 5.1 (s, 2H, N—CH$_2$), 5.8–9.4 (m, 14H, methyne-H, aromatic H and olefinic H)

Further compounds, inter alia the Examples 6b–6e listed in Table 3, were obtained in analogy to Example 6a.

TABLE 3

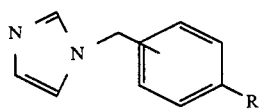

| Example | R = | characteristic $^1$H—NMR— signals, δ = | Rf silica gel |
|---|---|---|---|
| 6b | 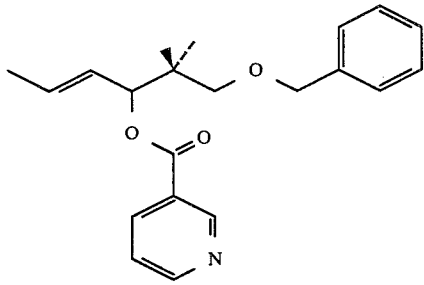<br>para | 1,1(d,6H,CH$_3$),<br>3,3(s,2H,OCH$_2$),<br>4,45(s,2H,OCH$_2$C$_6$H$_5$)<br>5,05(s,2H,N—CH$_2$)<br>5,7(d,1H,<br>6,3-9,3(m,18H,<br>aromat + olefin.<br>protons) | 0,32<br>CH$_2$Cl$_2$/<br>CH$_3$OH<br>= 20:1 |
| 6c | <br>para | 1,0-2,2(m,10H,<br>Cyclohexane-<br>methylene-H),<br>3,78(d,2H,<br>—CH$_2$O—)<br>6,0-9,3 (m,13H,<br>olefin and<br>aromat. H) | 0,19<br>ethyl acetate/<br>CH$_3$OH<br>= 20:1 |
| 6d | 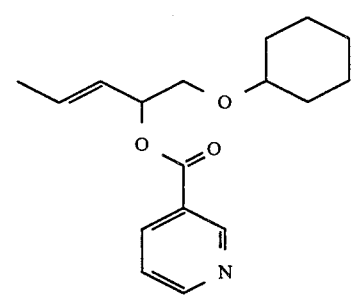<br>ortho | 1,1(d,6H,—CH$_3$),<br>3,3(s,2H,OCH$_2$),<br>4,5(s,2H,OCH$_2$Ph),<br>5,6(d,1H,Methyne-<br>H), 6,4-9,2 (m,<br>18H, olefin.<br>and aromat. H) | 0,35<br>CH$_2$Cl$_2$/<br>CH$_3$OH<br>= 20:1 |
| 6e | <br>meta | 0,8-1,8(m,9H,<br>Alkyl-H), 3,3-<br>3,8 (m,4H,<br>—CH$_2$OCH$_2$—), 5,7-<br>9,4 (m,14H,<br>Methyne-H, olefin.<br>H and aromat. H) | 0,2<br>ethyl acetate/<br>CH$_3$OH<br>= 10:1 |

EXAMPLE 7a

E-4-Pentyloxy-1-[4-(1-imidazolylmethyl)phenyl]but-1-en-3-yl benzyl ether 70 mg (1.6 mmol) of 55 percent NaH dispersion were initially introduced into 3 ml of dry dimethylformamide. At room temperature, 360 mg (1.1 mmol) of alcohol 5a in 3 ml of DMF were added, followed by 152 mg (1.2 mmol) of benzyl chloride in a little DMF. The mixture was stirred at room temp. for 18 h, water was added, and the mixture was extracted three times with toluene. Drying of the combined toluene phases over magnesium sulfate, removal of the solvent in vacuo and chromatography on silica gel (ethyl acetate) produced 200 mg (0.5 mmol, 45%) of benzyl ether 6a as a colorless liquid (TLC, EA/CH$_3$OH=10:1, Rf=0.36)

$^1$H NMR (60 MHz, CDCl$_3$): δ=0.66-2.0 (m, 9H, —((CH$_2$)$_3$CH$_3$), 3.33-3.66 (m, 4H, —H$_2$COCH$_2$—), 3.93-4.41 (m, 1H, methyne-H), 4.58 (d, 2H, —OCH$_2$—Ph), 5.08 (s, 2H, Im—CH$_2$—Ph), 5.9-7.6 (m, 14H, arom. H and olefin. H)

Further compounds, inter alia the Examples 7b–7f listed in Tab. 4, were obtained in analogy to Example 7a.

TABLE 4

[structure: imidazole-N-CH2-C6H4-R]

| Example | R = | characteristic ¹H—NMR-signals, δ = | Rf silica gel |
|---|---|---|---|
| 7b | [cyclohexyloxy/benzyloxy hexenyl, para] | 1,0–2,1(m, 10H, Cyclohexane-methylene-H), 3,4(m, 1H, Methyne-H), 3,6(d, 2H, OCH$_2$—), 4,1(m, 1H, Methyne-H), 4,6(d, 2H, Ph—CH$_2$O—), 5,1(s, 2H, N—CH$_2$—), 6,0–7,6(m, 14H, arom. H and olefin H) | 0.26 CHCl$_3$/CH$_3$OH = 20:2 |
| 7c | [cyclohexyloxy/pyridylmethyloxy hexenyl, para] | 1,0–2,1(m, 10H, Cyclohexane-methylene-H), 3,4(m, 1H, Methyne-H), 3,6(d, 2H, OCH$_2$—), 4,2(m, 1H, Methyne-H), 4,6("s", 2H, Ph—CH$_2$O), 5,1 (s, 2H, N—CH$_2$), 6,0–8,7(m, arom. H and olefin. H) | 0,14 ethyl acetate/CH$_3$OH = 20:2 |
| 7d | [butyloxy/pyridylmethyloxy hexenyl, para] | 0,7–1,9(m, 9H, —(CH$_2$)$_3$CH$_3$), 3,3–3,7(m, 4H, —CH$_2$OCH$_2$—), 4,0–4,5(m, 1H, Methyne-H), 4,6("s", 2H, —OCH$_2$Pyr) | 0,17 ethyl acetate/CH$_3$OH = 10:1 |
| 7e | [cyclohexyloxy/pyridylmethyloxy hexenyl, ortho] | 1,0–2,0(m, 10H, Cyclohexane-methylene-H), 3,4(m, 1H, Methyne-H), 3,6(d, 2H, OCH$_2$—), 4,1(m, 1H, Methyne-H), 4,6("s", 2H, PyrCH$_2$O—) | 0.18 ethyl acetate/CH$_3$OH = 20:1 |
| 7f | [butyloxy/benzyloxy hexenyl, meta] | 0,66–2,0(m, 9H, —(CH$_2$)$_3$CH$_3$), 3,3–3,6(m, 4H, —CH$_2$OCH$_2$—), 3,9–4,4(m, 1H, Methyne-H), 4,6(d, 2H, —OCH$_2$Ph) | 0,4 ethyl acetate/CH$_3$OH = 10:1 |

We claim:
1. A compound of the formula I

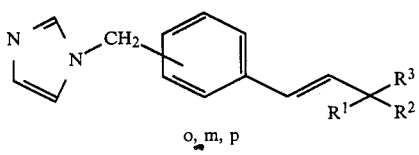

in which:

R$^1$ and R$^2$ together with the carbon atom to which they are attached denote a carbonyl group, or R$^1$ denotes hydrogen, and R$^2$ denotes the radical —OR$^4$, in which R$^4$ represents hydrogen, or
(a) a branched or unbranched alkanoyl radical having up to 10 carbon atoms,
(b) a benzylcarbonyl or benzoyl radical, the phenyl radical being unsubstituted or substituted one to three times with halogen or C$_1$–C$_4$-alkyl,
(c) the radical

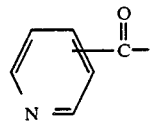

(d) branched or unbranched alkyl having 1–10 carbon atoms,
(e) a benzyl radical, the phenyl nucleus being unsubstituted or substituted one to three times with halogen or $C_1$–$C_4$-alkyl, or
(f) the radical

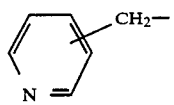

$R^3$ denotes a phenyl radical which can be substituted one to three times in the nucleus with halogen, trifluoromethyl or alkyl or alkoxy, each having 1–4 carbon atoms, the substituents being identical or different in the event of bi- or tri-substitution, or a cycloalkyl radical having 3–8 carbon atoms, a straight-chain or branched alkenyl radical having 3 to 8 carbon atoms, the alkyl or alkenyl radicals being unsubstituted or substituted with
(a) a straight-chain or branched alkoxy radical having up to 10 carbon atoms, or a cycloalkoxy radical having up to 6 carbon atoms, or a straight-chain or branched alkenyloxy or alkynyloxy radical having 3 to 6 carbon atoms,
(b) halogen, cycloalkyl having 3 to 7 carbon atoms, an unsubstituted phenyl, α- or β-thienyl or α- or β-furyl radical which in turn are substituted one to three times in the nucleus with halogen, trifluoromethyl or alkyl or alkoxy having 1–6 carbon atoms, the substituents being identical or different in the event of bi- or tri-substitution,
(c) an unsubstituted phenoxy, α- or β-thienyloxy or cycloalkoxy radical having 3 to 7 carbon atoms, or one of said radicals which in turn is substituted one to three times in the nucleus with halogen, trifluoromethyl or alkyl or alkoxy each having 1–6 carbon atoms, the substituents being identical or different in the event of bi- or tri-substitution, or
(d) a 1-imidazolyl radical.

2. A compound of the formula I as claimed in claim 1, in which
$R^1$ and $R^2$ together with the carbon atom to which they are attached denote a carbonyl group, or $R^1$ denotes hydrogen and $R^2$ denotes the radical —$OR^4$, in which $R^4$ represents hydrogen, or
(a) branched or unbranched alkanoyl having up to 6 carbon atoms,
(b) the benzylcarbonyl or benzoyl radical, the phenyl nucleus being unsubstituted or substituted once with fluorine, chlorine or methyl,
(c) the radical

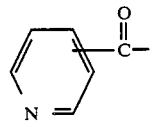

(d) branched or unbranched alkyl having 1–6 carbon atoms,
(e) the benzyl radical, the phenyl nucleus being unsubstituted or substituted once with chlorine, fluorine or methyl, or
(f) the radical

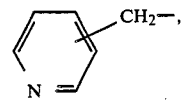

and
$R^3$ denotes a cycloalkyl radical having 3–8 carbon atoms, a straight-chain or branched alkyl radical having up to 8 carbon atoms, a straight-chain or branched alkenyl radical having 3 to 8 carbon atoms, the alkyl or alkenyl radicals being unsubstituted or substituted with
(a) a straight-chain or branched alkoxy radical having up to 6 carbon atoms, a cycloalkoxy radical having up to 6 carbon atoms, or a straight-chain or branched alkenyloxy or alkynyloxy radical having 3 to 6 carbon atoms,
(b) cycloalkyl having 3–7 carbon atoms, an unsubstituted phenyl, α- or β-thienyl or α- or β-furyl radical,
(c) an unsubstituted phenoxy, α- or β-thienyloxy or cycloalkoxy radical having 3–7 carbon atoms, or one of said radicals which in turn is substituted one to three times in the nucleus with halogen, trifluoromethyl or alkyl or alkoxy each having 1–4 carbon atoms, the substituents being identical or different in the event of bi- or tri-substitution, or
(d) a 1-imidazolyl radical.

3. A compound of the formula I as claimed in claim 1, in which
$R^1$ and $R^2$ together with the carbon atom to which they are attached denote a carbonyl group, or $R^1$ is hydrogen, and $R^2$ is the radical —$OR^4$, in which $R^4$ denotes hydrogen, benzyl, alklyl having 1–6 carbon atoms or the radical

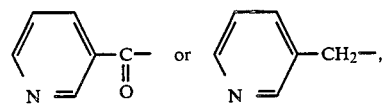

$R^3$ is a cycloaliphatic radical having 3–8 carbon atoms, a straight-chain or branched alkyl radical having up to 8 carbon atoms, a straight-chain or branched alkenyl radical having 3 to 8 carbon atoms, the alkyl or alkenyl radicals being unsubstituted or substituted with
(a) a straight-chain or branched alkoxy radical having up to 10 carbon atoms, (b) cycloalkyl having 3–7 carbon atoms, an unsubstituted phenyl α- or β-thienyl or α- or β-furyl radical, or a phenyl, thienyl or furyl radical,
(c) an unsubstituted phenoxy, α- or β-thienyloxy or cycloalkoxy radical having 3–7 carbon atoms, or
(d) a 1-imidazolyl radical.

4. A medicament which contains an effective amount of a compound of the formula I, as claimed in claim 1, mixed with one or both of a pharmaceutically customary vehicle or stabilizer, for the treatment of disorders where the tendency to platelet aggregation is increased.

5. The method which comprises administering to a mammal an effective amount of a compound of the formula I, or of a pharmaceutically acceptable acid addition salt thereof, for the treatment of disorders where the tendency to platelet aggregation is increased.

* * * * *